US012584095B2

(12) United States Patent
Bongiovanni et al.

(10) Patent No.: US 12,584,095 B2
(45) Date of Patent: Mar. 24, 2026

(54) EXTRACELLULAR VESICLES FROM MICROALGAE

(71) Applicants: CONSIGLIO NAZIONALE DELLE RICERCHE, Rome (IT); ATLANTIC TECHNOLOGICAL UNIVERSITY, Sligo (IE)

(72) Inventors: Antonella Bongiovanni, Palermo (IT); Mauro Manno, Palermo (IT); Gabriella Pocsfalvi, Naples (IT); Nicolas Touzet, Clarina (IE)

(73) Assignees: CONSIGLIO NAZIONALE DELLE RICHERCHE, Rome (IT); ATLANTIC TECHNOLOGICAL UNIVERSITY, Ballinode (IE)

( * ) Notice: Subject to any disclaimer, the term of this patent is extended or adjusted under 35 U.S.C. 154(b) by 826 days.

(21) Appl. No.: 17/787,189

(22) PCT Filed: Dec. 17, 2020

(86) PCT No.: PCT/EP2020/086622
§ 371 (c)(1),
(2) Date: Jun. 17, 2022

(87) PCT Pub. No.: WO2021/122880
PCT Pub. Date: Jun. 24, 2021

(65) Prior Publication Data
US 2023/0025620 A1      Jan. 26, 2023

(30) Foreign Application Priority Data
Dec. 18, 2019 (IT) ........................ 102019000024580

(51) Int. Cl.
| | |
|---|---|
| *C12N 1/12* | (2006.01) |
| *A61K 8/14* | (2006.01) |
| *A61K 47/46* | (2006.01) |
| *C12N 1/02* | (2006.01) |

(52) U.S. Cl.
CPC .................. *C12N 1/12* (2013.01); *A61K 8/14* (2013.01); *A61K 47/46* (2013.01); *C12N 1/02* (2013.01)

(58) Field of Classification Search
CPC .................................... C12N 1/12; A61K 8/14
See application file for complete search history.

(56) References Cited

U.S. PATENT DOCUMENTS 9,273,359 B2      3/2016   Gho et al.

FOREIGN PATENT DOCUMENTS

| | | |
|---|---|---|
| EP | 2519635 B1 | 11/2018 |
| WO | 2011090731 A1 | 7/2011 |
| WO | 2013070324 A1 | 5/2013 |
| WO | 2013138335 A1 | 9/2013 |
| WO | 2014134132 A1 | 9/2014 |
| WO | 2016166716 A1 | 10/2016 |
| WO | 2017161010 A1 | 9/2017 |

OTHER PUBLICATIONS https://en.wikipedia.org/wiki/PDCD6IP (Year: 2025).*
International Search Report and Written Opinion for International Patent Application No. PCT/EP2020/086622, mailed Apr. 7, 2021, 10 pages.
Long Huan et al., Comparative Analysis of Ciliary Membranes and Ectosomes, Current Biology, Nov. 17, 2016, pp. 3327-3335, vol. 26, No. 24, Elsevier Ltd., GB.
Wood Christopher R. et al., The Cilium Secretes Bioactive Ectosomes, Current Biology, Apr. 25, 2013, pp. 906-911, vol. 23, No. 10, Elsevier Ltd., GB.
De La Pena Milagros R. et al, Cell growth, effect of filtrate and nutritive value of the tropical Prasinophyte *Tetraselmis tetrathele* (Butcher) at different phases of culture, Aquaculture Research, Nov. 1, 2005, pp. 1500-1508, vol. 36, No. 15, John Wiley & Sons Ltd., GB.
Davis M. E. et al., Nanoparticle therapeutics: an emerging treatment modality for cancer, Nature Reviews, Drug Discovery, Sep. 2008, pp. 771-782, vol. 7, Macmillan Publishers Limited, US.
Shi J. et al., Nanotechnology in Drug Delivery and Tissue Engineering: From Discovery to Applications, Nano Letters, Sep. 8, 2010, pp. 3223-3230, vol. 10, Issue 9, American Chemical Society, US.
Simons M. et al., Exosomes—vesicular carriers for intercellular communication, Current Opinion in Cell Biology, Aug. 2009, pp. 575-581, vol. 21, Issue 4, Elsevier Ltd.
Yanez-Mo M. et al., Biological properties of extracellular vesicles and their physiological functions, Journal of Extracellular Vesicles, published online May 14, 2015, vol. 4:27066, Informa UK Limited, Taylor & Francis Group.
Thery C. et al., Minimal information for studies of extracellular vesicles 2018 (MISEV2018): a position statement of the International Society for Extracellular Vesicles and update of the MISEV2014 guidelines, Journal of Extracellular Vesicles, published online Nov. 23, 2018, vol. 7:1535750, Informa UK Limited, Taylor & Francis Group.
Leyland B. et al., Are Thraustochytrids algae?, Fungal Biology, Oct. 2017, pp. 835-840, vol. 121, Issue 10, Elsevier.
Konoshenko M. Y. et al., Isolation of Extracellular Vesicles: General Methodologies and Latest Trends, BioMed Research International, Jan. 30, 2018, Article ID 8545347, 27 pages, vol. 2018, Hindawi, GB.

(Continued)

*Primary Examiner* — Ruth A Davis
(74) *Attorney, Agent, or Firm* — Armstrong Teasdale LLP

(57)      ABSTRACT

Extracellular vesicles derived from native, photosynthetic, non-fermenting microalgae are provided. A method for isolating extracellular vesicles from native, photosynthetic, non-fermenting microalgae involving growth, centrifugation and ultracentrifugation steps is also provided. Use of the isolated extracellular vesicles as carriers for delivering diagnostic, therapeutic, nutraceutic and/or cosmetic agents is further provided.

4 Claims, 4 Drawing Sheets

(56)             References Cited

OTHER PUBLICATIONS

Kowal J. et al., Proteomic comparison defines novel markers to characterize heterogeneous populations of extracellular vesicle subtypes, PNAS, published online Feb. 8, 2016, pp. E968-E977, vol. 113, No. 8, Proceedings of the National Academy of Sciences of the United States of America, US.

Biller J. S. et al., Bacterial vesicles in marine ecosystems, Science, Jan. 10, 2014, pp. 183-186, vol. 343, AAAS, Washington D.C., US.

Kooijmans A. A. et al., Exosome mimetics: a novel class of drug delivery systems, International Journal of Nanomedicine, Mar. 15, 2012, pp. 1525-154, vol. 2012:7, Dove Medical Press Ltd., GB.

Mentkowski K. I. et al., Therapeutic Potential of Engineered Extracellular Vesicles, AAPS Journal, Mar. 15, 2018, vol. 20(3):50, American Association of Pharmaceutical Scientists, US.

Lener T. et al., Applying extracellular vesicles based therapeutics in clinical trials—an ISEV position paper, Journal of Extracellular Vesicles, Dec. 31, 2015, vol. 4:30087, Taylor & Francis Group.

Kim O. Y. et al., Extracellular vesicle mimetics: Novel alternatives to extracellular vesicle-based theranostics, drug delivery, and vaccines, Seminars in Cell & Developmental Biology, Jul. 2017, pp. 74-82, vol. 67, Elsevier.

Armstrong J. P.K., Re-Engineering Extracellular Vesicles as Smart Nanoscale Therapeutics, ACS Nano, Jan. 24, 2017, pp. 69-83, vol. 11, Issue 1, American Chemical Society, US.

Blanch Harvey W., Bioprocessing for biofuels, Current Opinion in Biotechnology, pp. 390-395, vol. 23, Issue 3, Jun. 2012, Elsevier B.V.

Khozin-Goldberg I. et al., Microalgae as a Source for VLC-PUFA Production, in: Nakamura Y. et al., Lipids in Plant and Algae Development, Subcellular Biochemistry, Mar. 30, 2016, pp. 471-510, Chapter 19, vol. 86, Springer International Publishing, CH.

Ryu B.-G. et al., Microalgae-mediated simultaneous treatment of toxic thiocyanate and production of biodiesel, Bioresource Technology, Apr. 2014, pp. 166-173, vol. 158, Elsevier.

Pulz O. et al., Valuable products from biotechnology of microalgae, Applied Microbiology and Biotechnology, Aug. 6, 2004, pp. 635-648, vol. 65, Springer.

* cited by examiner

A

B

C

EXTRACELLULAR VESICLES FROM MICROALGAE

CROSS-REFERENCE TO RELATED APPLICATIONS

This application is a National Stage Application of International Patent Application No. PCT/EP2020/086622, having an International Filing Date of Dec. 17, 2020, which claims priority to Italian Patent Application No. 102019000024580 filed Dec. 18, 2019, the entire contents of each of which are hereby incorporated by reference herein.

FIELD OF THE INVENTION

The present invention relates to a method of obtaining extracellular vesicles (EVs) from microalgae, the extracellular vesicles (EVs) obtained by the method of the invention as well as the use of the microalgae-derived EVs as nanocarriers for the delivery of diagnostic, therapeutic, nutraceutic and/or cosmetic agents.

BACKGROUND OF THE INVENTION

Microalgae are a polyphyletic group of eukaryotic microorganisms known as protists. Several species of microalgae are used as a human food source or nutritional supplement. There has been a drive in the last decade in better exploiting the metabolic attributes of microalgae with respect to high-value compounds such as natural antioxidants (for example, carotenoid pigments or polyunsaturated omega-3 fatty acids) or antimicrobial compounds.

Microalgae are also extensively researched in the context of renewable third-generation biofuels due to their lipid content and their bioremediation capacities for the depuration of a variety of waste streams.

The exploitation of the silica exoskeleton of some species, such as diatoms, as nano-based mechanisms to deliver drugs has also been attempted.

Extracellular vesicles (EVs) are cell-derived, membranous structures that mediate intercellular communication by transferring biomolecules such as proteins and RNA between cells [Davis M E, et al., Nat Rev Drug Discov (2008) 7(9); Shi J, et al., Nano Lett (2010) 10(9); Simons M, Raposo G Curr Opin Cell Biol (2009) 21; Yanez-Mo M, et al., J Extracell Ves (2015) 4]. Théry and Witwer et al. (2018) recently revised the required parameters for the robust description of EVs [Théry C, et al. Minimal information for studies of extracellular vesicles 2018 (MISEV2018): a position statement of the International Society for Extracellular Vesicles and update of the MISEV2014 guidelines, Journal of Extracellular Vesicles. 2018; 7:1. DOI: 10.1080/20013078.2018.1535750.]. In MISEV2018, the EV identity is described in terms of protein composition (including presence of ALIX), size (("small EVs" (sEVs) and "medium/large EVs" (m/lEVs), with ranges defined, for instance, respectively, <200 nm [small], or >200 nm [large and/or medium])), morphology (round-shaped), and density (≤1.2 g/ml).

Cellular, organismal, inter-organismal and even inter-species cell-to-cell communication via EVs is intensively studied in basic science with high expectation for a large variety of derived biotechnological applications.

WO2017161010A1 and WO2014134132A1 disclose the production of membrane vesicles from EVs and organelles from human cells and bovine milk, respectively.

U.S. Pat. No. 9,273,359 discloses Gram-positive bacterial vesicles.

WO2013138335A1 discloses Gram-negative bacteria (i.e. cyanobacteria) secreted lipid-containing vesicles, and in some embodiments, methods that further include the collection of protein-containing vesicles.

WO02013070324A1 and WO2016166716A1 disclose edible plant-derived nanovesicles.

The uses of extracellular vesicles disclosed in the prior art include various applications for human health (WO2017161010A1, WO2014134132A1, U.S. Pat. No. 9,273,359, WO02013070324A1, WO2016166716A1) and as a source of renewable biofuels (in particular, the cyanobacteria-derived vesicles of WO2013138335A1).

EP 2519635 B1 (WO2011090731) discloses *Schizochytrium* extracellular bodies comprising extracellular vesicles. However, the review Leyland B, Leu S, Boussiba S (2017) Are Thraustochytrids algae? Fungal Biology 121: 835-840, discusses whether Thraustochytrids, which *Schizochytrium* belongs to, can be designated as algae. According to the authors of Leyland et al. (2017), "The term 'algae' is used to refer to a polyphyletic assemblage of organisms which are photosynthetic. Other criteria sometimes cited include the reliance on chlorophyll a as a primary pigment, oxygen production, lack of vascular tissues, and reproductive cells which do not possess a sterile covering or protection (Committee 1994; Lee 1999; South & Whittick 2009; Bolton 2017; Sanders 2017)". As such, the authors review a body of scientific evidence to assert that: "Thraustochytrids are not algae because they are not photosynthetic and lack a plastid".

Furthermore, EP 2519635 B1 (WO2011090731) describes an approach which is based on the transformation of *Schizochytrium* to synthesise a viral protein, creating a Genetically Modified Organism (GMO), which is then cultivated under dark fermentation conditions with the addition of organic nutrients as the main source of carbon. EP 2519635 B1 (WO2011090731) does not disclose the ability of non-engineered *Schizochytrium* cells to produce extracellular bodies; it only does so for the transformed mutant type. Indeed, EP 2519635 B1 (WO2011090731) is directed to the production of a viral (including but not limited to influenza virus A) heterologous polypeptide which, in some embodiments, is expressed in the host "extracellular bodies". The transgenic proteins expressed in fermenting *Schizochytrium* cells are hemagglutinine (HA), neuraminidase (NA), glycoprotein, envelope protein (E), fusion protein (F), matrix protein (M), glycoprotein (G) and glycoproteins gp120 and gp41. In some embodiments (0146) the transgenic proteins include type I, type II, multipass, lipid and GPI anchored membrane proteins. These proteins, in some embodiments, are expressed in an "extracellular body" defined as a vesicle, a micelle, a membrane fragment a membrane aggregate or mixture thereof. As one example, FIG. 4B shows the Coomassie stained recombinant HA proteins recovered from the 60% sucrose fraction. The density of the 60% sucrose fraction is 1.286 g/ml. This indicates that the recombinant HA proteins were recovered from the extracellular medium at a density value which is higher than the density value at which EVs are usually recovered. Maria Yu. Konoshenko, Evgeniy A. Lekchnov, Alexander V. Vlassov, Pavel P. Laktionov, "Isolation of Extracellular Vesicles: General Methodologies and Latest Trends", BioMed Research International, vol. 2018, Article ID 8545347, 27 pages, 2018. https://doi.org/10.1155/2018/8545347, in fact disclose that EVs are characterized by a density between 1.13-1.19 g/ml.

The finding that EVs may be used as natural carriers of bioactive small molecules and proteins has raised great interest in the drug delivery field given that such vesicles could find promising applications for therapeutic delivery of miRNA, siRNA, mRNA, lncRNA, proteins, peptides and synthetic drugs.

Over the last three decades, a variety of nanoparticle-based drug delivery systems have been developed, including synthetic polymer- and lipid-based nanoparticles, as well as other organic and inorganic material-based nanovectors [Kowal J, et al. PNAS (2016) 113; Biller, S J, et al., Science (2014) 343:183].

It is believed that natural EVs could potentially overcome some of the limitations of synthetic liposomes [Kooijmans, S. A., et al., Int J Nanomedicine, (2012) 6; Mentkowski K I., The AAPS Journal (2018) 20:508]. Indeed, EVs intrinsically possess many attributes of a drug delivery vehicle, since they are well tolerated in the body, as evidenced by their wide distribution in various biological fluids; have a long circulating half-life; are internalized by other cells; are capable of carrying small molecules and cargoes; and are able to cross the blood brain barrier (BBB).

Recently, native and drug-loaded mammalian cell (e.g., mesenchymal cell)-derived EVs have been developed and now constitute a rapidly growing research field known as "cell-free therapy". Phase I clinical trials with dendritic cell-derived EVs have demonstrated feasibility and short-term safety of autologous EV administration (Lener et al., J Extracell Vesicles. 2015; 4: 10.3402/jev.v4.30087).

However, the systemically delivered EVs of the prior art tend to accumulate in the liver, kidneys and spleen and some mammalian-derived secreted EVs have shown limited pharmaceutical acceptability because of their source, in particular bovine milk derived EVs. Furthermore, despite the appreciable success of synthetic or natural nanomaterials as delivery systems, technical challenges involving their large-scale, cost-effective production and intrinsic toxicity have limited to date their clinical and market translation.

The use of microalgae as a natural source for extracellular vesicles would provide a number of advantages. Indeed, the metabolic attributes of microalgae are actively researched worldwide to address strategic priorities, with a particular focus on biofuel generation, bioremediation developments and biosynthesis of high-added value biochemical [Yanez-Mo M, et al., J Extracell Ves (2015) 4; Kim, O. Y., et al., Semin Cell Dev Biol, (2017). 67; Armstrong, J. P., et al. ACS Nano, (2017) 11(1); Blanch, H. W., Curr Opin Biotechnol, (2012). 23(3); Khozin-Goldberg, I., et al., Sub-cell Biochem, (2016). 86; Ryu, B. G., et al., Bio-resour Technol, (2013). 129; Pulz, O. and W. Gross, Appl Microbiol Biotechnol, (2004). 65(6)]. Microalgal biomass is used world-wide for human nutrition, animal feed, aquaculture and biofertilisation, with a market size of ~5,000 t/year of dry matter generating a turnover in excess of ~US$ 1.25 billion. Recent advances in microalgal biotechnology have generated much optimism for a viable industrial production of microalgae-derived compounds such as antioxidants or omega-3 polyunsaturated fatty acids. Extracellular nanovesicles from microalgae disclosed here would offer a number of advantages compared to mammalian cell-derived EVs in that they have high growth rates and can be cultured on non-arable land under controlled environmental conditions in large scale photobioreactors. In addition, their natural and sustainable origin with probably greater societal acceptance (and less risky in terms of ethics) as a source for formulation preparations, especially when considering functional foods and cosmetic sectors make them an ideal source of EVs.

However, the possibility to isolate extracellular vesicles form microalgae was neither previously known nor suggested in the prior art.

Indeed, microalgae are unicellular organisms for which mechanisms of secretion of extracellular vesicles are known in the prior art only in relation to primary and motile cilia/flagella. For example, in the green alga *Chlamydomonas reinhardii* these extracellular vesicles, named ectosomes, are derived from the flagellar membrane and are involved in flagellar resorption. The description of EVs obtained from photosynthetic microalgal sources has not been previously reported. Some unicellular organism of the Chlorophyte phylum related to land plants have a reduced, substantial or peculiarly ornamented cell wall, as in the case of *Chlamydomonas*. It was expected in the prior art that the existence of a rigid cell wall would prevent the secretion of extracellular vesicles. Other examples are Diatoms and Dinoflagellates, for which the person skilled in the art would expect that the presence of a silica exoskeleton and/or cell wall of varying thickness or other ornaments outside the plasma membranes (eg. thecae of armored Dinoflagellates), would make them less suitable as possible candidates for EV production.

SUMMARY OF THE INVENTION

The present inventors now surprisingly found that photosynthetic microalgae, with varying organization of their cell walls, including species belonging to, but not limited to, the Diatom and Chlorophyte lineages, naturally release EVs into growth media. To the inventors' knowledge, this is the first description of such membranous vesicles produced by photosynthetic microalgae. Significantly, the mechanism(s) underlying this ability allows exploiting the EV potential as membranous bio-nanomaterials, wherein the microalgal EVs are collected from the culture medium without the need to harvest the cells. The use of these organisms (some being generally regarded as safe GRAS for consumption) as producers of delivery vehicles has not been explored so far and will open new avenues for nanobiotechnology.

SUMMARY OF THE INVENTION

Accordingly, a first aspect of the present invention is a novel product, i.e. extracellular vesicles obtainable from native, photosynthetic, non-fermenting microalgae.

In the present description, the extracellular vesicles derived or obtainable from native, photosynthetic, non-fermenting microalgae according to the invention are sometimes referred to as "nanoalgosomes".

The disclosure of EP 2519635 B1 (WO201109073) cited above as prior art considerably differs from extracellular vesicles of the present invention, which are Alix-positive extracellular vesicles obtained from native, non-GMO, photosynthetic and non-fermenting microalgal organisms.

The extracellular vesicles of the present invention were made available through a novel method designed by the present inventors for isolating extracellular vesicles from microalgae, which is a second aspect of the present invention.

As it will be illustrated in the experimental section, the native, photosynthetic, non-fermenting microalgae-derived EVs of the present invention are recovered in a continuous gradient at $1.12\pm0.01$ g/ml and $1.16\pm0.1$ g/ml fractions which, as mentioned above, is the typical density value at which EVs are usually recovered.

A third aspect of the invention is the use of the microalgae-derived EVs as biogenic-nanocarriers for the molecular delivery of diagnostic, therapeutic, nutraceutic and/or cosmetic agents.

Further features and advantages of the invention are also described.

DETAILED DESCRIPTION

Figure 1:
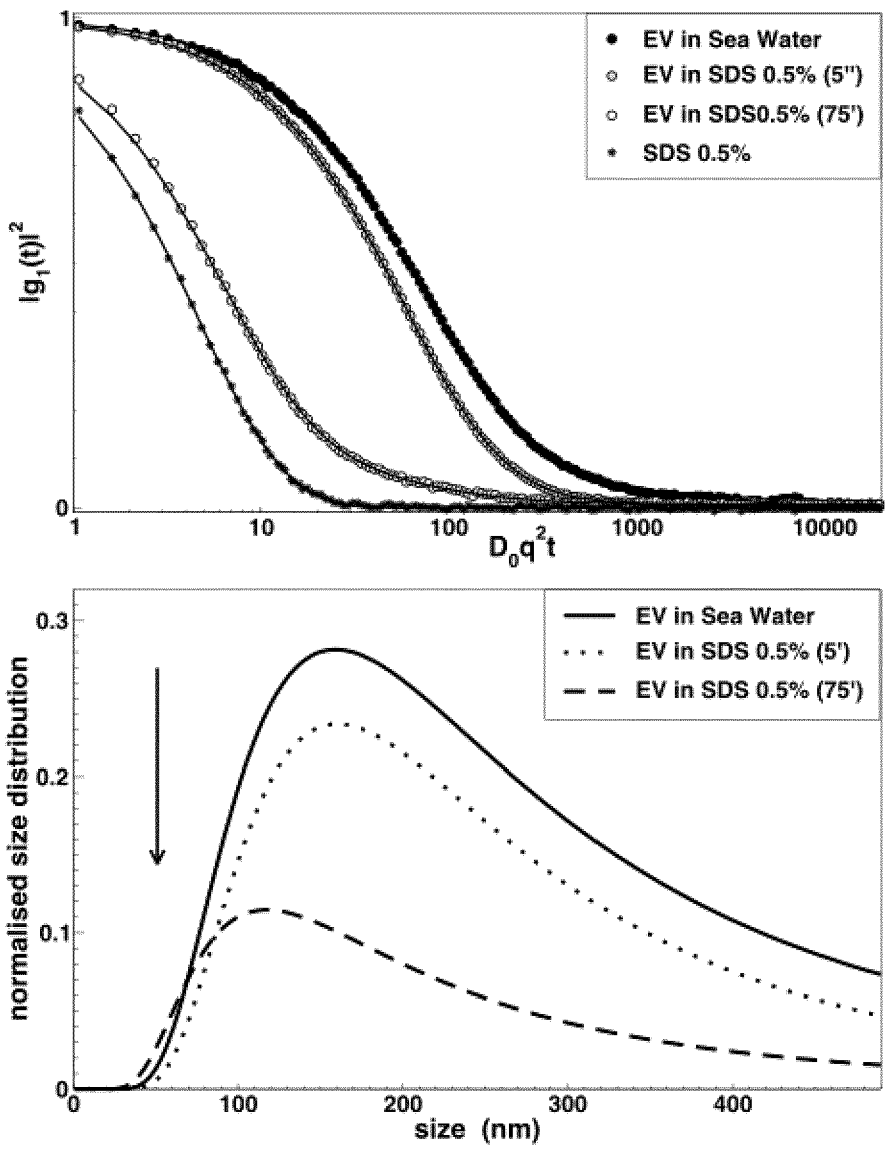
FIG. 1 is a graph reporting the results obtained with the Diatom *Odontella* sp. (LA-CW-28) derived sEVs by Dynamic Light Scattering (DLS) experiments on CW-28 Nanovesicles.

The microalgae-derived EVs of the present invention have a particle size comprised between 50 and 300 nm (small extracellular vesicles (sEV), obtainable by ultracentrifugation) or comprised between 300 nm and 2 μm (large extracellular vesicles (lEV), obtainable by low-velocity centrifugation). They contain the established extracellular vesicle protein marker Alix, and optionally the protein markers enolase and/or actin. As experimentally demonstrated by their sensitivity to the detergent sodium dodecyl sulfate (SDS), the microalgae-derived EVs of the invention are biogenic lipidic membranous nanovesicles with a lipidic bilayer membrane.

As it will be further illustrated herein below, the microalgae-derived EVs of the present invention are isolated from the conditioned media of microalgal cultures, such as, but not limited to, the marine, photosynthetic Diatom *Odontella* sp. or the Chlorophyte *Tetraselmis* sp.

The novel product is obtainable by the method of the present invention, which comprises the following steps:

a) inoculating a photosynthetic microalgal culture medium with a microalgal biomass inoculum at a final concentration of from 0.5 to 2 mg per ml of wet biomass;

b) cultivating the inoculated microalgal biomass with illumination provided by a LED lighting system at about 30-200 microEinstein per second and square meter ($\mu E\ m^{-2}\ s^{-1}$), whereby microalgae-derived extracellular vesicles are produced;

c) isolating a first fraction of microalgae-derived extracellular vesicles from the microalgae culture of step b) by a first separation step including low-velocity centrifugation, whereby a pellet containing microalgae-derived extracellular vesicles and a low-velocity supernatant are obtained; and d) isolating a second fraction of microalgae-derived extracellular vesicles from the low-velocity supernatant obtained in step c), by a second separation step including ultracentrifugation, whereby a pellet containing further microalgae-derived extracellular vesicles is obtained.

A detailed description of the isolation method of the present invention is provided herein below. The following detailed description is provided by way of illustration only and is not intended to limit the scope of the present invention, which is determined by the appended claims.

1. Microalgal Cultivation

Step a): Inoculation

The microalgal culture media (filter-sterilized f/2 or BG11 media for marine and freshwater species) are inoculated with a microalgal biomass inoculum at a final concentration of 0.5 to 1.5 mg per ml of wet biomass at beginning of experiments (concentration in cultivation vessel on day-0) for a final volume of 0.1-15 liters in a glass flasks or cylindrical reactor. The final total volume may be scaled up and down according to the desired yield.

Step b): Growth

The inoculated microalgal biomass are maintained under controlled temperature (13-22° C., preferably 17° C.) and photoperiod conditions (14:10 light:dark) and for a predetermined period of time (10-50 days, preferably 30 days), with illumination provided by a LED lighting system at about 30-200 microEinstein per second and square meter ($\mu E\ m^{-2}\ s^{-1}$) (preferably 100 $\mu E\ m^{-2}\ s^{-1}$).

In a typical batch system the growth dynamics are monitored typically over a duration of 10-50 days, preferably 30 days, in the cultures using a well plate spectrophotometer, an electronic particle counter, gravimetry or light microscopy as appropriate. The temperature and the photoperiod may be varied to optimize growth in different species of microalgae, and different measurements may be used to monitor cell growth. Modulation of cultivation parameters will affect quality and quantity of EVs produced.

Steps c) and d): Isolation of Microalgae-Derived Extracellular Vesicles

An essential step of the method of the present invention is to separate the extracellular vesicles from the microalgal cells and culture supernatant containing soluble secreted materials comprising but not limited to secreted proteins, metabolites and the molecular components of microalgae culture medium. Different separation procedures based on different physical principles, i.e. filtration, centrifugation, precipitation may in principle be applied. Preferentially, differential centrifugation for the isolation of extracellular vesicles (EVs) from a microalgae culture. Differential centrifugation is composed of a series of centrifugation steps with increasing velocity to remove cells, cellular debris and to obtain the fraction containing micro vesicles at the end of low-velocity centrifugation and smaller EVs containing fraction at the end of ultracentrifugation step. This step is essential to the isolation procedure; indeed, the velocity and time of centrifugation are critical. For instance, if the initial centrifugation velocity is too high, cell can lyse and contaminate the sample.

Step c): Low Velocity Centrifugation

Low-velocity centrifugation is preferably performed by at least three separate centrifugation steps at increasing velocity. The velocity (range 200-15000×g), number of the centrifugation steps (range 1-10 steps, preferably 6 steps), temperature (range 2-20° C., preferably 4° C.), type of rotor (fixed angle or swingout rotors, preferably swinging bucket rotors), tube and centrifuge employed in the low velocity centrifugation step may vary. Preferably, the first low-velocity centrifugation step is performed at the velocity of 300×g, at 4° C. for 10 min in swinging bucket rotors. The second low-velocity centrifugation step is preferably performed at 2,000×g at 4° C. for 10 min. The third low-velocity centrifugation step is preferably performed at 10,000×g at 4° C. for 30 min. Preferably, each low velocity centrifugation steps is performed two times. Pellets are obtained by careful decantation. Alternatively, in some instances, the supernatant can be removed by aspiration with the help of pipette. Pellets resulting from the last low velocity centrifugation step at 10,000×g contain the larger extracellular vesicles (e.g., microvesicles). Preferably, the 10,000×g pellet is washed two times with an appropriate buffer. Generally, PBS buffer filtered through a 20 nm sterile filter is employed. Washing steps are performed by careful resuspension of the pellet followed by re-centrifugation using the conditions used for obtaining the pellet itself.

Step d): Ultracentrifugation

Ultracentrifugation of the 10,000×g supernatant of step c) is performed in order to obtain a fraction containing the smaller EVs. Ultracentrifugation is preferably performed at 118,000×g (range 100,000-120,000×g) using swinging bucket rotors at 4° C. for 2 h, but the duration of the centrifugation may vary (range 1-24 hours). Preferably, a washing step is performed using the preferred buffer in which the pellet is carefully resuspended. The supernatant is usually removed by careful decantation but, in some instances, it may be removed by aspiration. After ultracentrifugation, the pellet may be resuspended in generally low volume of buffer.

Although the disclosed product has been obtained by using differential ultracentrifugation, other fractional isolation methods could in principle be used to separate small EVs (e.g. tangential flow fractionation, gradient ultracentrifugation).

Within the present description, the terms "extracellular vesicles" or "EVs" is used with reference to both large (e.g., microvesicles) and small extracellular vesicles E.G., exosomes, ectosomes).

The term "microalgae" is usually used to indicate any eukaryotic microscopic algae, typically found in freshwater or marine systems, living in both the water column and sediment. They are unicellular species which exist individually, or in chains or groups. Microalgae include, for example but are not limited to, photosynthetic Diatoms, Dinoflagellates, Haptophytes or Chlorophytes.

Furthermore, within the present description the term "microalgae" is used to indicate photosynthetic microalgae including, for example, species with silica exoskeleton and/or ornamented cell walls and with promising antioxidant or antimicrobial activities or signatures of pigments and fatty acids for example but not limited to the Chlorophyte Haematococcus pluvialis, diatom Stauroneis sp., Haptophyte Pavlova sp. or the model species Chlamydomonas reinhardtii. Further examples of microalgae include the Chlorophyte Tetraselmis sp. (such as the strain Tetraselmis sp. LA-CW-02) and the Diatom Odontella sp. (such as the strain Odontella sp. LA-CW-28).

The production method of the present invention differs from other EV-related methods of the prior art in that its focus is targeted to nanovesicles refined for the first time from unicellular eukaryotic, photosynthetic microalgae. In addition, irrespective of their content, the goal of the invention is also to produce microalgae-derived EVs in a large amount for industry application/s. This aim could not be achieved with mammalian cell-derived EVs, which are conversely indicated for different purposes which require low amount of EVs, including personalized cell-free therapy.

The method of the present invention advantageously allows to generate a broad range of new products based on membranous biogenic nanomaterials (i.e., EVs) from a sustainable and renewable bioresource (i.e., microalgae), which can be used as new natural delivery system for high-value microalgal substances (such as antioxidants, pigments, lipids and complex carbohydrates), bioactive biological molecules (e.g., proteins, miRNA, siRNA, mRNA, lncRNA, peptides) and/or synthetic drugs.

The following experimental part is provided by way of illustration only and is not intended to limit the scope of the invention as defined by the appended claims.

EXPERIMENTAL PART

Samples of marine photosynthetic Chlorophyte (strain Tetraselmis sp. LA-CW-02) and Diatom (strain Odontella sp. LA-CW-28) including cellular pellets and conditioned media were used. Cell pellets were solubilized in RIPA buffer and small and large extracellular vesicles (exosomes and microvesicles) were isolated by ultracentrifugation from the conditioned media.

Microalgal strains are grown for 30 days in triplicate glass tubes containing 60 ml of filter-sterilized medium. All the cultures are subjected to a photoperiod of 14:10 (light:dark) under an irradiance of 60-70 $\mu E\ m^{-2}\ s^{-1}$. The corresponding conditioned media are processed at the end of the microalgal cultivation as follows:

Series of low speed centrifugation rounds (300×g and 2,000×g) to remove cells and large organic agglomerates. The biogenic extracellular nanoparticles are recovered by 10,000×g (large EVs) and 118,000×g (small EVs) centrifugation using swinging bucket rotors at 4° C. for 2 h.

EV protein content measured by microbicinchoninic (BCA) colorimetric assay. To examine the size distribution of microalgal EVs, Dynamic Light Scattering (DLS) analyses of sEVs was applied. Scattered light intensity and its time autocorrelation function g2(t) were measured simultaneously on different EV samples at T=20° C. using a Brookhaven BI-9000 correlator (Brookhaven Instruments, Holtsville, NY, USA) equipped with a solid-state laser tuned to λ0=532 nm. The samples were diluted to a final total protein content of 50 μg/ml in order to avoid vesicle interaction and multiple scattering artefacts. Lipid bilayer presence was assessed by treating sEV preparation with SDS and analyzing the sEV size distribution following detergent treatment. EV morphology was assessed by Atomic force microscopy (AFM).

Results: Starting from a conditioned media volume of 60 ml and a final microalgal biomass of 1.5 mg/ml the following product content is obtained, in terms of total small extracellular vesicle protein amount: CW-02 small extracellular vesicle total proteins=8+2 μg, CW-28 small extracellular vesicle total proteins=3+0.7 μg.

DLS analyses (FIG. 1) demonstrated that membranous nanovesicles (sensitive to SDS) of 50-350 nm in size (moda of 160 nm) are present in the sEV preparation.

Figure 3:
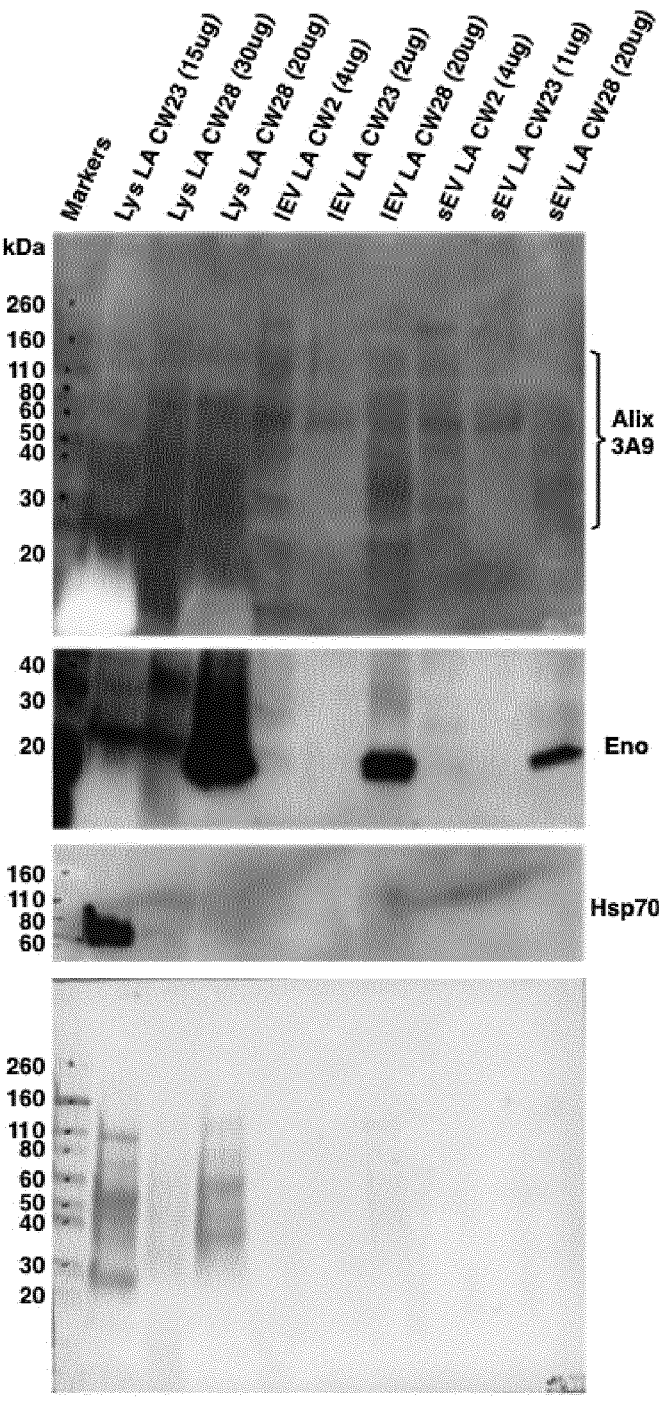
FIG. 3 shows western blot images obtained by using established antibodies.

FIG. 3 shows a representative image of immunoblot analyses of lysates (Lys) of the microalgal strains (LA CW2, LA CW23, LA CW28), large EV fraction (lEV), small EV fractions (sEV). The loaded protein amount is indicated in each lane. EVs positive for an EV protein marker (e.g., Alix) were isolated from the microalgal conditioned-media.

The results obtained are illustrated in the appended drawings, in which:

FIG. 1 shows the results obtained with the Diatom Odontella sp. (LA-CW-28) derived sEVs by Dynamic Light Scattering (DLS) experiments on CW-28 Nanovesicles. The upper panel shows the intensity autocorrelation functions for sEVs, sEVs after incubation with 0.5% SDS and the reference 0.5% SDS solution; the functions are analyzed to derive the size distributions; the lower panel shows the size distributions normalized to the initial amount of sEVs. sEV samples have been measured in the buffer used for their resuspension (Phosphate Buffer Saline, PBS, with 0.5M NaCl) or upon addition of SDS (to a final concentration of 0.5%). SDS affects the concentration of sEVs upon incubation, confirming the lipid composition of microalgae-derived nanovesicles membrane.

Figure 2:
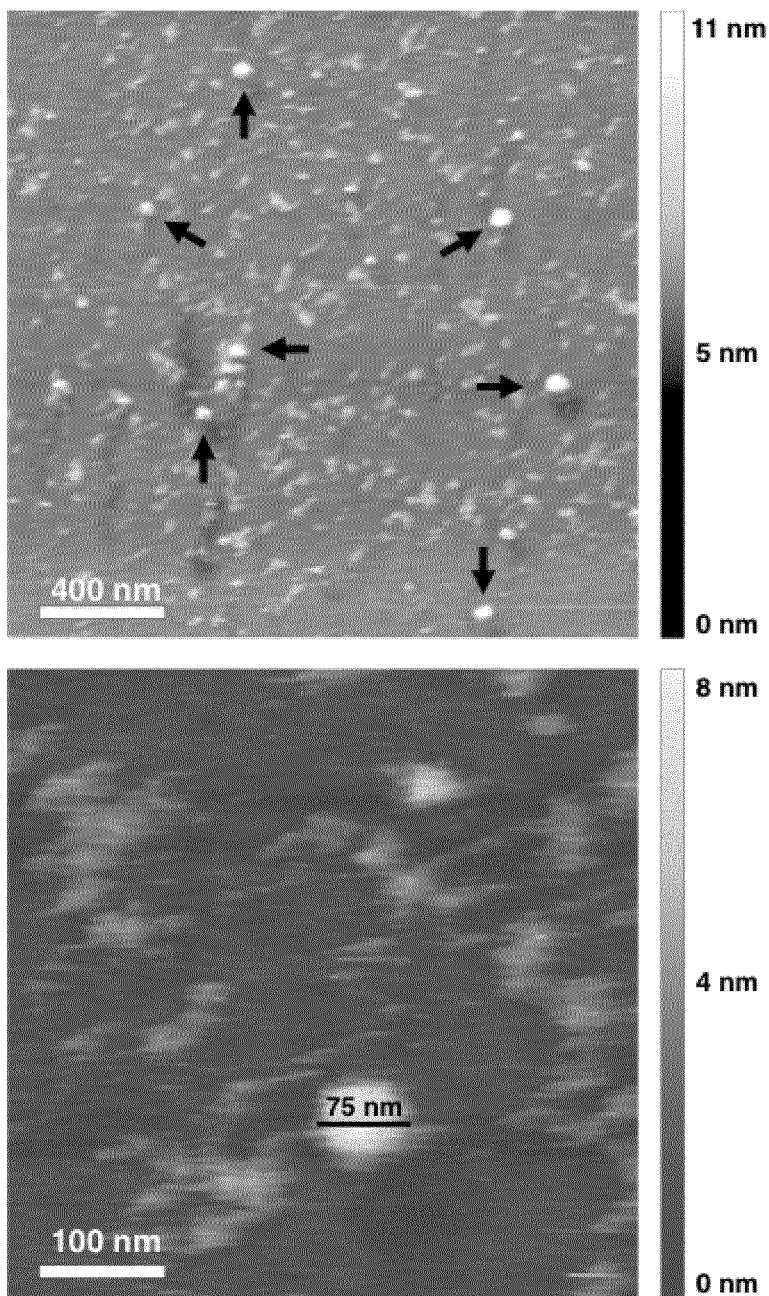
FIG. 2 shows Atomic Force Microscopy (AFM) images on Chlorophyte *Tetraselmis* sp. (LA-CW-02) derived sEVs.

FIG. 2 shows Atomic Force Microscopy (AFM) images on Chlorophyte *Tetraselmis* sp. (LA-CW-02) derived sEVs. AFM images (in tapping mode) of sEVs from microalgae (100 times dilution and 10 minutes incubation on mica sample substrate). The upper panel displays a large field 2 μm image, where many round-shaped EVs can be observed (marked by arrows) with a size between 40 and 100 nm. The lower panel displays a close-up 500 nm image displaying in more detail a sEV of 75 nm.

FIG. 3 shows the results obtained from western blot analysis using established antibodies. Immunoblots of total protein extracts (Lys), large vesicles (lEV) and small vesicles (sEV) from LA CW2, LA CW23, LA CW28 microalgae strains using specific antibody recognizing an EV marker (anti-Alix, clone 3A9), and anti-Enolase and anti-Hsp70. The lower panel shows the Ponceau red stained PVDF membrane, as loading control.

Figure 4:
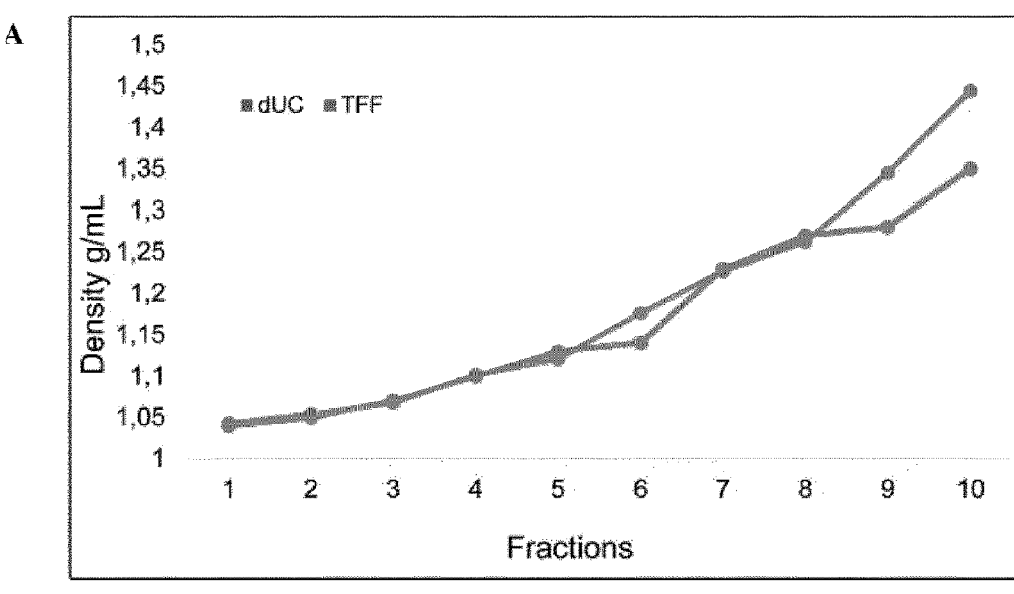
FIG. 4 is a graph reporting the results of experiments using Iodixanol gradient to determine the nanoalgosome density; also shown are representative immunoblot images from nanoalgosomes isolated by dUC, and loaded on iodixanol density gradient.
Figure 4:
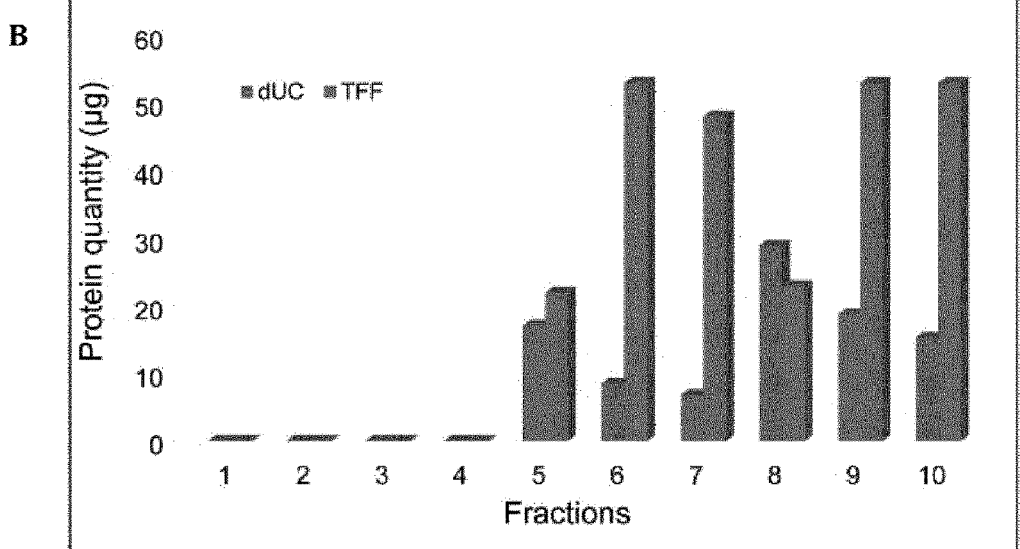
Figure 4:
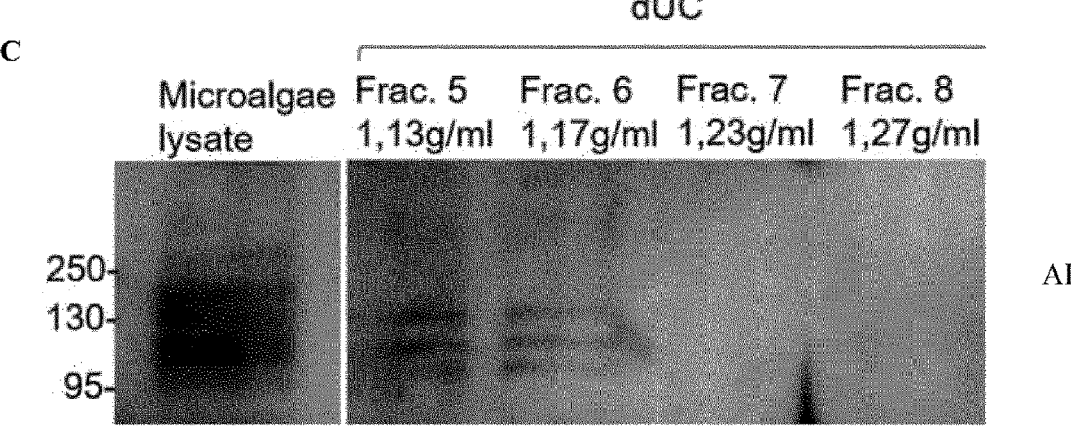

FIG. 4 shows the results of experiments using Iodixanol gradient to determine the nanoalgosome density. (A) The density of the ten fractions measured in the gradient ultracentrifugation (gUC) of dUC-isolated samples. (B) The quantity of protein measured in each gUC fraction. (C) Representative immunoblot analyses of nanoalgosomes isolated by dUC, and loaded on iodixanol density gradient. 20 μg of microalgae lysate and equal fraction volumes were loaded on gel. Fraction 5 of dUC-separated nanoalgosomes and at a less extent the fraction 6 are positive for EV specific biomarkers (Alix). Two independent technical replicas (n=2) were performed.

What is claimed is:

1. An extracellular vesicle (EV) derived from a microalga, wherein the extracellular vesicle (EV) is a biogenic lipidic membranous nanovesicle having a particle size ranging from 50 to 300 nm, being a small extracellular vesicle (sEV) or from 300 nm to 2 μm, being a large extracellular vesicle (lEV) and comprises a lipidic bilayer membrane, and wherein the extracellular vesicle (EV) is derived from a native, photosynthetic, non-fermenting microalga and contains at least the extracellular vesicle protein marker Alix and one or more protein markers selected from the group consisting of enolase, actin and any combination thereof.

2. The extracellular vesicle (EV) of claim 1, wherein the microalga is selected from photosynthetic microalgal phyla Chlorophytes and Bacillariophytes.

3. The extracellular vesicle (EV) of claim 1, wherein the microalga is selected from the photosynthetic microalgal divisions Euglenophyta, Cryptophyta, Rhodophyta, Glaucophyta, Chromophyta and Chlorophyta.

4. The extracellular vesicle (EV) of claim 1, wherein said extracellular vesicle (EV) is used as a carrier for delivering a diagnostic, therapeutic, nutraceutic and/or cosmetic agent.

\* \* \* \* \*